(12) United States Patent
Gliner et al.

(10) Patent No.: US 11,684,302 B2
(45) Date of Patent: *Jun. 27, 2023

(54) AUTOMATED GRAPHICAL PRESENTATION OF ELECTROPHYSIOLOGICAL PARAMETERS

(71) Applicant: Biosense Webster (Israel) Ltd., Yokneam (IL)

(72) Inventors: Vadim Gliner, Haifa (IL); Alexander Salevich, Haifa (IL); Yair Palti, Herzelia (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 334 days.

This patent is subject to a terminal disclaimer.

(21) Appl. No.: 16/714,046

(22) Filed: Dec. 13, 2019

(65) Prior Publication Data

US 2021/0177294 A1 Jun. 17, 2021

(51) Int. Cl.
*A61B 5/349* (2021.01)
*A61B 34/20* (2016.01)
(Continued)

(52) U.S. Cl.
CPC .......... *A61B 5/349* (2021.01); *A61B 1/00004* (2013.01); *A61B 1/00045* (2013.01);
(Continued)

(58) Field of Classification Search
CPC ......... A61B 5/349; A61B 5/283; A61B 34/20; A61B 1/00004; A61B 1/00045; A61B 2034/2046

See application file for complete search history.

(56) References Cited

U.S. PATENT DOCUMENTS

| 5,391,199 A | 2/1995 | Ben-Haim |
|---|---|---|
| 6,239,724 B1 | 5/2001 | Doron et al. |

(Continued)

FOREIGN PATENT DOCUMENTS

| WO | WO 96/05768 A1 | 2/1996 |
|---|---|---|
| WO | 2015/026733 A1 | 2/2015 |
| WO | 2020/185339 A1 | 9/2020 |

OTHER PUBLICATIONS

Extended European Search Report dated Apr. 15, 2021, from corresponding European Application No. 20213321.1.

*Primary Examiner* — Catherine M Voorhees
*Assistant Examiner* — Roland Dinga
(74) *Attorney, Agent, or Firm* — Troutman Pepper Hamilton Sanders LLP

(57) ABSTRACT

A medical apparatus includes a probe configured for insertion into a body of a patient. The probe includes electrodes configured to contact tissue of a region within the body. The apparatus further includes a display screen, a position-tracking system configured to acquire position coordinates of the electrodes within the body, and a processor. The processor is configured to acquire electrophysiological signals from the electrodes while they are held stationary in the region, extract electrophysiological parameters from the signals, compute a measure of consistency of the parameters, and render to the display screen a three-dimensional (3D) map of the tissue while superimposing on the map, responsively to the position coordinates, a visual indication of the extracted parameters at the locations for which the measure of consistency satisfied a consistency criterion, and automatically discarding from the map the parameters for which the measure of consistency did not satisfy the consistency criterion.

12 Claims, 3 Drawing Sheets

(51) Int. Cl.
*A61B 5/283* (2021.01)
*A61B 1/00* (2006.01)

(52) U.S. Cl.
CPC .............. *A61B 5/283* (2021.01); *A61B 34/20* (2016.02); *A61B 2034/2046* (2016.02)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2010/0268059 A1 | 10/2010 | Ryu et al. |
| 2012/0184858 A1 | 7/2012 | Harlev et al. |
| 2014/0371615 A1 | 12/2014 | Narayan et al. |
| 2015/0057507 A1* | 2/2015 | Koyrakh ................ A61B 5/066 600/301 |
| 2015/0119738 A1 | 4/2015 | Deno |
| 2016/0045123 A1* | 2/2016 | Bar-Tai ................ A61B 5/349 600/515 |
| 2016/0106336 A1* | 4/2016 | Li ........................ A61B 5/0536 600/374 |
| 2017/0311833 A1 | 11/2017 | Afonso et al. |
| 2018/0042505 A1* | 2/2018 | Botzer ................ A61B 5/352 |
| 2018/0132743 A1 | 5/2018 | Markovitz |

* cited by examiner

AUTOMATED GRAPHICAL PRESENTATION OF ELECTROPHYSIOLOGICAL PARAMETERS

FIELD OF THE INVENTION

The present invention relates generally to electrophysiological measurements, and particularly to apparatus and methods for automated mapping of electrophysiological parameters.

BACKGROUND

An electrophysiological (EP) map of a tissue of a patient is generated by positioning one or more electrodes on a region of the tissue, acquiring an EP signal of the region, and then repeating the process for a different region. EP parameters are extracted from the EP signals in each region of measurement, and then displayed over an image of the tissue.

SUMMARY

Embodiments of the present invention that are described hereinbelow provide improved methods and apparatus for mapping of electrophysiological parameters.

There is therefore provided, in accordance with an embodiment of the present invention, a medical apparatus, which includes a probe configured for insertion into a body of a patient, wherein the probe includes one or more electrodes configured to contact tissue of a region within the body. The apparatus further includes a display screen, and a position-tracking system configured to acquire position coordinates of the one or more electrodes within the body, and a processor. A processing unit is configured to acquire respective electrophysiological signals from the one or more electrodes while the one or more electrodes are held stationary at respective locations in the region over at least a preset length of time, to extract respective electrophysiological parameters from the electrophysiological signals acquired by the one or more electrodes at the respective locations, and to compute a respective measure of consistency of the respective electrophysiological parameters extracted from the electrophysiological signals acquired by the electrodes over the preset length of time at each of the respective locations.

The processing unit is further configured to render to the display screen a three-dimensional (3D) map of the tissue while superimposing on the map, responsively to the position coordinates, a visual indication of the extracted electrophysiological parameters at the respective locations for which the respective measure of consistency satisfied a predefined consistency criterion, and to discard automatically from the map the electrophysiological parameters for which the respective measure of consistency did not satisfy the predefined consistency criterion.

In a disclosed embodiment, the electrophysiological parameter includes a local activation time (LAT) in a heart of the patient, and the measure of consistency is indicative of a variation of the LAT. Additionally or alternatively, the measure of consistency includes a peak-to-peak variation of the LAT at any given location, and the consistency criterion requires that the peak-to-peak variation of the LAT not exceed a predefined limit.

In another embodiment, the electrophysiological parameter includes an electrophysiological voltage, and the measure of consistency is indicative of a variation of the electrophysiological voltage. Additionally or alternatively, the measure of consistency includes a peak-to-peak variation of the electrophysiological voltage at any given location, and the consistency criterion requires that the peak-to-peak variation of the electrophysiological voltage not exceed a predefined limit.

In yet another embodiment, the 3D map is rendered in a background color, and the visual indication includes other colors superimposed on the background color at the respective locations to indicate a value of the extracted electrophysiological parameter.

There is also provided, in accordance with an embodiment of the present invention, a method for electrophysiological mapping. The method includes acquiring respective electrophysiological signals from one or more electrodes on a probe in contact with tissue of a region within a body of a patient while the one or more electrodes are held stationary at respective locations in the region over at least a preset length of time and while acquiring position coordinates of the one or more electrodes. Respective electrophysiological parameters are extracted from the electrophysiological signals acquired by the one or more electrodes at the respective locations, and a respective measure of consistency is computed of the respective electrophysiological parameters extracted from the electrophysiological signals acquired by the electrodes over the preset length of time at each of the respective locations. The method further includes displaying a three-dimensional (3D) map of the tissue while superimposing on the map, responsively to the position coordinates, a visual indication of the extracted electrophysiological parameters at the respective locations for which the respective measure of consistency satisfied a predefined consistency criterion, and automatically discarding from the map the electrophysiological parameters for which the respective measure of consistency did not satisfy the predefined consistency criterion.

The present invention will be more fully understood from the following detailed description of the embodiments thereof, taken together with the drawings in which:

DETAILED DESCRIPTION OF EMBODIMENTS

Overview

Figure 1:
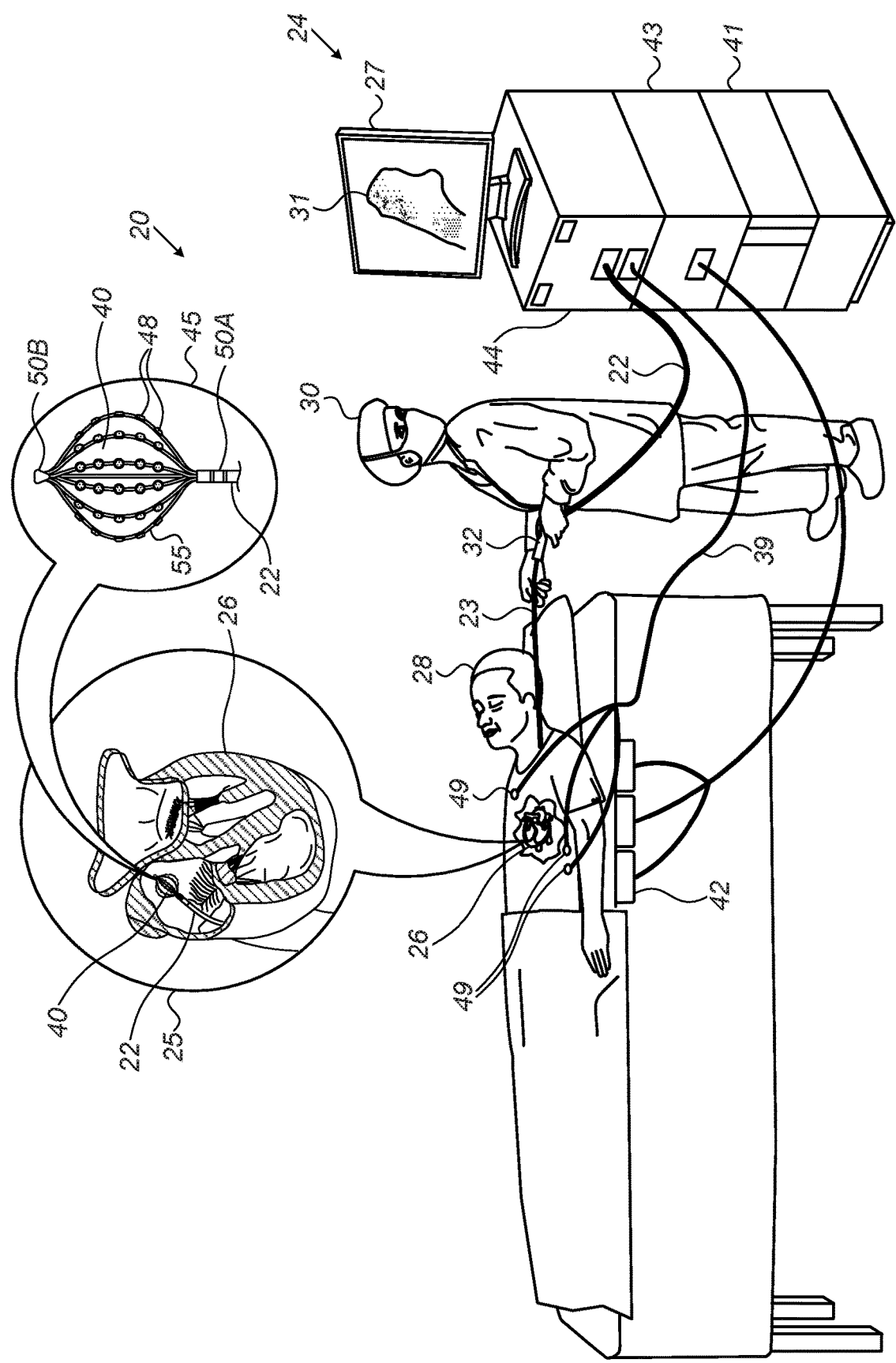
FIG. 1 is a schematic pictorial illustration of a medical apparatus for mapping an EP parameter in a heart of a patient, in accordance with an embodiment of the present invention.

Generating an electrophysiological (EP) map of a tissue of a patient involves positioning one or more electrodes on a region of the tissue, acquiring the signal of the region, and then repeating the process for a different region. When small numbers of electrodes are used, this process generates accurate maps of the EP parameters extracted from these signals, since the physician can observe the acquired signals, and only accept "good" signals (as judged by the physician) into the map. A good signal is typically generated only when the electrode is in good contact with the tissue. Using a small number of electrodes has, however, the drawback that the mapping takes a long time.

For catheters with large numbers of electrodes, the mapping time is reduced, but the accuracy is decreased, since the physician is incapable of properly inspecting all the simultaneously generated signals within the available time. The task of accepting good signals (and rejecting others) may be facilitated by presenting to the physician the analyzed results of the signals, i.e., the values of an EP parameter across the measured region. (For the sake of brevity, "value of an EP parameter" will in the following description be referred to simply as "EP parameter.") The task may be further facilitated by presenting these values in a graphical form, such as a map of the values. However, the physician is still required to use his/her subjective judgement in accepting or rejecting the analyzed results, with an inherent variability in the acceptance due to subjectivity. Moreover, requiring the physician to judge the quality of these results will further tax his/her time and attention during the mapping procedure, especially if a large number of electrodes is used.

The embodiments of the present invention that are described herein address these problems by providing a medical apparatus comprising a probe, a display screen, a position-tracking system, and a processor. The probe, which comprises one or more electrodes, is inserted into a body of a patient so that it contacts tissue within the body. While the probe and its electrodes are held stationary on the tissue over a preset length of time, the position-tracking system acquires the position coordinates of the electrodes, and the processor acquires EP signals from the electrodes. The processor extracts the respective EP parameters from the signals, and computes a measure of consistency of the values at each electrode location. The processor renders to the display screen a three-dimensional (3D) map of the tissue while superimposing on the map a visual indication of the extracted EP parameters at the locations for which the measure of consistency satisfied a predefined consistency criterion. The processor automatically discards from the map the EP parameters for which the respective measure of consistency did not satisfy the predefined criterion.

This approach facilitates rapid automated decisions as to the points on the tissue where the acquired EP parameters are valid, without having to rely on a subjective and time-consuming assessment by the physician.

In a disclosed embodiment, the processor displays a 3D map of a chamber of the heart in which EP parameter is being mapped. The 3D map is presented in a neutral color tone or monotone color, such as gray. The EP parameter may comprise, for example, a local activation time (LAT) measured in the myocardium or a bipolar or unipolar maximum voltage. LAT is the time interval between a reference time determined, for example, from the body surface ECG or intracardiac electrogram, and the time of the local depolarization event. Other useful scalar functions of the physiological parameters, may be calculated and displayed, superposed on a combined display of LAT (as pseudocolor) and propagation velocity (as arrows). One such useful scalar function is the range of voltages measured at each sampled point (displayed as a pseudocolor): an abnormally low range is diagnostic of scar tissue, upon which the conduction velocity may be displayed as arrows. LAT can be determined manually (and usually automatically by the CARTO® system) by marking one or more of (a) the maximum negative slope of the voltage of the unipolar recording (−dV/dt); (b) maximum absolute voltage of the bipolar recording, (c) the maximum absolute slope dV/dt of the bipolar recording or (d) minimum voltage of the bipolar recording.

During the measurement, the processor extracts the EP parameters over several (for example 3-7) heartbeats, and keeps updating the 3D map for each heartbeat, by superimposing onto the map an indication of the EP parameters. This indication may be, for example, a color code, wherein the lowest value of the EP parameter is denoted by blue, the highest by red, and the intermediate values by the colors of the visible spectrum between blue and red. The 3D map may be updated after each heartbeat based on the last measured EP parameters or on a cumulative average of the EP parameters. Alternatively, the 3D map may be updated only after the EP parameters have been measured over the several heartbeats, and then only with the points that pass the criterion for consistency, as described below.

The processor also computes a measure of consistency for the EP parameter over these several heartbeats, reflecting the variation of the extracted values over the heartbeats. The criterion applied to the measure of consistency may require, for example, that the variation be no greater than a certain threshold, for example a voltage threshold. When the variation exceeds this threshold at a given measurement point on the tissue, the measured EP parameter at this point is rejected, and the corresponding area on the 3D map is displayed in its neutral background color.

System Description

FIG. 1 is a schematic pictorial illustration of a medical apparatus 20 for mapping an EP parameter in a heart 26 of a patient 28, in accordance with an embodiment of the present invention.

A physician 30 navigates a basket catheter 40, seen in detail in an inset 45, to a target location in heart 26 of patient 28, by manipulating a shaft 22, using a manipulator 32 near the proximal end of the catheter, and/or deflection from a sheath 23. In the embodiment seen in an inset 25, physician 30 uses catheter 40 to perform electro-anatomical mapping of a cardiac chamber. EP signals are acquired from tissue by using electrodes 48 on basket catheter 40 touching the tissue, as further detailed below.

Catheter 40 is inserted in a collapsed configuration, through sheath 23, and only after the catheter exits sheath 23 does the catheter expand to its intended functional shape, as shown in inset 45. By containing catheter 40 in a collapsed configuration, sheath 23 also serves to minimize vascular trauma on its way to the target location.

Basket catheter 40 incorporates a magnetic sensor 50A, seen in inset 45, at the distal edge of shaft 22 (i.e., at the proximal edge of basket catheter 40). Typically, although not necessarily, sensor 50A is a Triple-Axis Sensor (TAS), comprising three miniature coils oriented in different directions. In the pictured embodiment, a second magnetic sensor 50B is incorporated in a distal edge of the basket catheter. Sensor 50B may be a Single-Axis Sensor (SAS) or a Triple-Axis Sensor (TAS), for example. Alternatively, catheter 40 may comprise other sorts of magnetic sensors, at these or other locations.

Catheter 40 further comprises multiple expandable spines 55, which may be mechanically flexible, to each of which are coupled multiple electrodes 48 for a total of, for example, 120 electrodes. Electrodes 48 are configured to touch the tissue of patient 28 for sensing EP signals. Magnetic sensors 50A and 50B and electrodes 48 are connected by wires running through shaft 22 to various processing circuits in a console 24.

Alternatively, apparatus 20 may comprise other types of catheters, with other sorts of electrode arrays, such as an inflatable balloon catheter with electrodes 48 on its outer surface.

Medical apparatus 20 comprises a magnetic-sensing subsystem for determining the position and orientation of basket catheter 40, and thereby the positions of electrodes 48. Patient 28 is placed in a magnetic field generated by a pad containing magnetic field generator coils 42, which are driven by a tracking module 43 in console 24. The magnetic fields generated by coils 42 give rise to electrical signals in sensors 50A and 50B, which are indicative of the position and/or orientation of the sensors. The signals form sensors 50A and 50B are transmitted back to tracking module 43, which converts the signals to corresponding digital inputs to a processor 41. Processor 41 uses these inputs to calculate the position and orientation of basket catheter 40 and thus to find the respective location of each of electrodes 48.

Methods of position and/or orientation sensing using external magnetic fields and magnetic sensors, such as sensors 50A and 50B, are implemented in various medical applications, for example, in the CARTO® system, available from Biosense Webster, Inc. (Irvine, Calif.). Such methods are described in detail in U.S. Pat. Nos. 5,391,199, 6,690, 963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Alternatively or additionally, apparatus 20 may use other methods of position sensing to find the locations of electrodes 48. For example, processor 41 may map the locations of electrodes 48 by measuring impedances between electrodes 48 and body-surface electrodes 49, which are placed on the chest of patient 28 and connected to console 24 by leads 39.

Processor 41 additionally receives electrophysiological signals via electrical interface 44, and uses the information contained in these signals together with the coordinates provided by magnetic sensors 50A and 50B to construct an electro-anatomical map 31 of the chamber of heart 26 in which catheter 40 is located. During and/or following the procedure, processor 41 may render electro-anatomical map 31 to a display screen 27.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables the processor to perform the disclosed steps, as described below.

The example illustration shown in FIG. 1 is chosen purely for the sake of conceptual clarity. FIG. 1 shows only elements related to the disclosed techniques for the sake of simplicity and clarity. Medical apparatus 20 typically comprises additional modules and elements that are not directly related to the disclosed techniques, and thus are intentionally omitted from FIG. 1 and from the corresponding description. The elements of medical apparatus 20 and the methods described herein may be further applied, for example, to control an ablation of tissue of heart 26.

Figure 2:
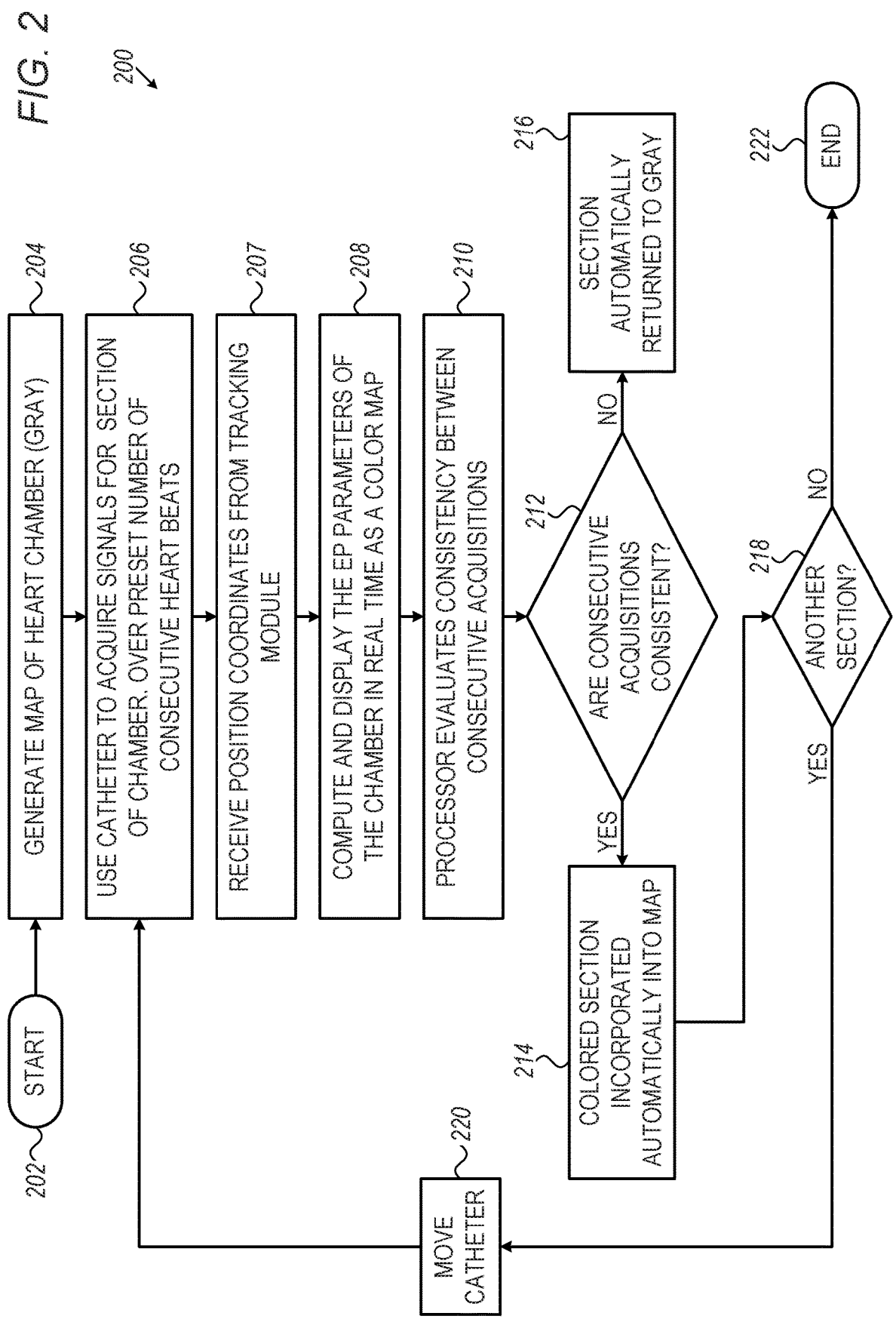
FIG. 2 is a flowchart that schematically illustrates a method for automated EP mapping, in accordance with an embodiment of the invention.

FIG. 2 is a flowchart 200 that schematically illustrates an automated process for EP mapping, in accordance with an embodiment of the invention. In this method, only EP parameters satisfying a certain consistency criterion are incorporated in the map. The embodiment shown in flowchart 200 refers to an example of acquiring EP signals from a chamber of heart 26 (with reference to FIG. 1). In alternative embodiments, the values of EP parameters may be acquired using other sorts of mapping apparatus, not only from the heart, but also from other organs and tissue, as will be apparent to those skilled in the art after reading the present description.

The process illustrated by flowchart 200 begins in a start step 202. In a map generation step 204, a uniformly gray (or other suitable background color) 3D map of the heart chamber is generated by processor 41 and rendered onto display screen 27. The 3D map is generated, for example, from an image of heart 26 previously stored in the processor, or based on position measurements taken by a catheter. Alternatively, the 3D map may be generated concurrently with displaying the EP parameters. In an acquisition step 206, processor 41 receives signals from electrodes 48, which are in contact with myocardial tissue in a part of a chamber of heart 26, over a preset number of consecutive heartbeats. Typically, the signals are acquired over a sequence of 3-7 heartbeats, but larger numbers of heartbeats may alternatively be sampled. In a tracking step, processor 41 receives signals from tracking module 43, and computes the respective location coordinates of electrodes 48.

In a computation and display step 208, processor 41 extracts the EP parameters separately for each heartbeat from the signals received in acquisition step 206. The processor displays the parameters by applying a corresponding color code to the appropriate region of the 3D map generated in step 204, based on the position coordinates received in tracking step 207. The color-coding may comprise, for example, showing the lowest values of the EP parameter as a blue color, the highest values as a red color, and intermediate values between the lowest and highest values in the same order as colors in a visible spectrum. However, other color-coding schemes, as well as shading or symbols, such as are known in the art, may alternatively be used. The EP parameters may be displayed at this step either as the last measured results or as a cumulative average. Alternatively, the color coding may be superimposed on the 3D map after the EP parameters have been measured over the several heartbeats, and then only with the points that pass the criterion for consistency, as applied in the following steps.

In a consistency evaluation step 210, processor 41 evaluates a measure of consistency of the EP parameters from heartbeat to heartbeat against a predefined consistency criterion. For the sake of brevity, EP parameters for which the measure of consistency satisfies the consistency criterion are also termed "consistent EP parameters" in the description that follows, whereas those parameters that do not satisfy the consistency criterion are termed "inconsistent EP parameters." The measure of consistency, as well as the consistency criterion, are defined in the present embodiment in terms of the peak heartbeat-to-heartbeat variation of the EP parameters.

In a first decision step 212, based on the outcome of consistency evaluation step 210, processor 41 decides whether the EP parameter decides satisfies the consistency criterion. For example, when the EP parameter computed in step 208 is the local activation time (LAT), the consistency criterion can be taken as a range of ±10 ms, i.e., if the LATs measured for each heartbeat over 3-7 heartbeats are within 20 ms of each other, they are considered to satisfy the consistency criterion. An another example, when the EP parameter is a bipolar or unipolar maximum voltage in the signals sensed by electrodes 48, the consistency criterion can be taken as a range of 20 mV, so that measured maximum voltages within this range are considered to satisfy the consistency criterion. Alternatively, larger or smaller ranges of the parameters can be taken as the consistency criterion.

Further alternatively, other sorts of consistency criteria can be applied. For example, processor 41 may compute the mean value of the EP parameter in question and the variance of the parameter over the sequence of heartbeats, and may define the consistency criterion in terms of the maximal acceptable variance.

When processor 41 finds that the EP parameter has satisfied the consistency criterion at step 212, it automatically incorporates the color-coded section in the 3D map, in an incorporation step 214. Alternatively, when the consistency criterion is not satisfied, the processor returns the area of the map in question to the background color, in a removal step 216.

In a second decision step 218, physician 30 decides whether EP signals need to be sampled from an additional region of the heart chamber. If the answer is affirmative, the physician moves basket catheter 40 to another region, and the EP signals from that region are measured, starting with acquisition step 206. Alternatively, when the EP values were rejected in first decision step 212, physician 30 may decide to re-sample the signals from that region. When no more EP signals need to be sampled, the process ends in an end step 222.

Figure 3C:
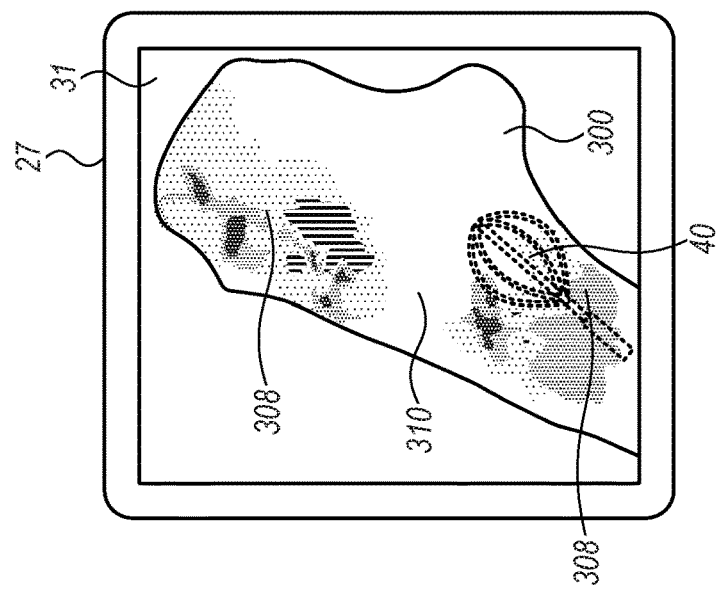
FIGS. 3A-3C are schematic illustrations of an electroanatomical map, comprising a 3D map of a chamber of a heart, with a superimposed visual indication of EP parameters during a measurement and after an automatic removal of inconsistent EP parameters, in accordance with an embodiment of the invention.
Figure 3B:
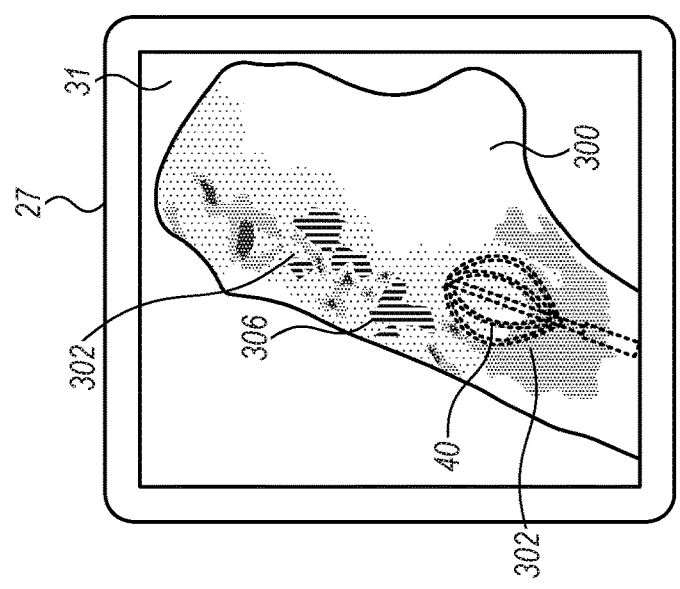
Figure 3A:
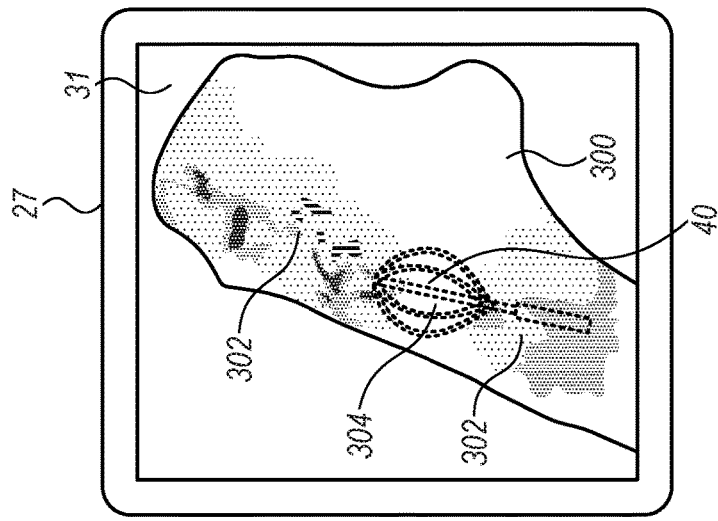

FIGS. 3A, 3B and 3C are schematic illustrations of electro-anatomical map 31, comprising a 3D map 300 of a chamber of heart 26, with a superimposed visual indication of the EP parameters during a measurement and after an automatic removal of inconsistent EP parameters, in accordance with an embodiment of the invention. Map 300 is initially colored in gray on display screen 27, and the color is updated in accordance with the method of FIG. 2 in various stages of the measurement using basket catheter 40, as is detailed below.

In FIG. 3A, a colored overlay 302 is superimposed on 3D map 300 as a visual indication of the EP parameters resulting from computation and display step 208. In FIG. 3A, colored overlay 302 may comprise both consistent and inconsistent values. Basket catheter 40 is positioned over an area 304, but the gray color of the area indicates that no EP parameters have yet been measured in this area.

FIG. 3B shows 3D map 300 with a colored overlay 306 now superimposed on area 304 of FIG. 3A, indicating the values of the measured EP parameters.

FIG. 3C shows 3D map 300 with only consistent EP parameters superimposed on it as a colored overlay 308. Inconsistent values of the measured EP parameters have now been removed in removal step 216 (FIG. 2) from an area 310, so that this area is displayed in the gray color of map 300. Thus, physician 30 will see only colored overlay 308 representing consistent EP parameters. The rejection of inconsistent EP parameters has been done automatically by processor 41, without any involvement by physician 30.

Although in the disclosed embodiment the EP parameters were measured from heart 26, in alternative embodiments the described method of automated acceptance or rejection of EP parameters may be applied other tissue of the body of patient 28. Moreover, in alternative embodiments more than one type of EP parameter may be measured and displayed simultaneously.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
a probe configured for insertion into a body of a patient and comprising one or more electrodes configured to contact tissue of a region within the body;
a display screen;
a position-tracking system configured to acquire position coordinates of the one or more electrodes within the body; and
a processor configured to:
acquire respective electrophysiological signals from the one or more electrodes while the one or more electrodes are held stationary at respective locations in the region over a preset number of consecutive heartbeats;
extract respective electrophysiological parameters from the electrophysiological signals acquired by the one or more electrodes at the respective locations;
compute a respective measure of consistency of the respective electrophysiological parameters extracted from the electrophysiological signals acquired by the electrodes over the preset number of consecutive heartbeats, the respective measure of consistency comprising a variation range; and
render to the display screen a three-dimensional (3D) map of the tissue while superimposing on the map, responsively to the position coordinates, a visual indication of the extracted electrophysiological parameters at the respective locations for which the variation range of the respective measure of consistency is smaller than a predefined range of a predefined consistency criterion, and automatically discarding from the map the electrophysiological parameters in the preset number of consecutive heartbeats for which the variation range of the respective measure of consistency is larger than the predefined range of the predefined consistency criterion.

2. The medical apparatus according to claim 1, wherein the electrophysiological parameter comprises a local-activation-time in a heart of the patient, and the measure of consistency is indicative of a variation of the local-activation-time.

3. The medical apparatus according to claim 2, wherein the measure of consistency comprises a peak-to-peak variation of the local-activation-time at any given location, and the consistency criterion requires that the peak-to-peak variation of the local-activation-time not exceed a predefined limit.

4. The medical apparatus according to claim 1, wherein the electrophysiological parameter comprises an electrophysiological voltage, and the measure of consistency is indicative of a variation of the electrophysiological voltage.

5. The medical apparatus according to claim 4, wherein the measure of consistency comprises a peak-to-peak variation of the electrophysiological voltage at any given location, and the consistency criterion requires that the peak-to-peak variation of the electrophysiological voltage not exceed a predefined limit.

6. The medical apparatus according to claim 1, wherein the 3D map is rendered in a background color, and the visual indication comprises other colors superimposed on the background color at the respective locations to indicate a value of the extracted electrophysiological parameter.

7. A method for electrophysiological mapping, the method comprising:
    acquiring respective electrophysiological signals from one or more electrodes on a probe in contact with tissue of a region within a body of a patient while the one or more electrodes are held stationary at respective locations in the region over at least a preset number of consecutive heartbeats and while acquiring position coordinates of the one or more electrodes;
    extracting respective electrophysiological parameters from the electrophysiological signals acquired by the one or more electrodes at the respective locations;
    computing a respective measure of consistency of the respective electrophysiological parameters extracted from the electrophysiological signals acquired by the electrodes over the preset number of consecutive heartbeats at each of the respective locations, the respective measure of consistency comprising a variation electrophysiological parameter value; and
    displaying a three-dimensional (3D) map of the tissue while superimposing on the map, responsively to the position coordinates, a visual indication of the extracted electrophysiological parameters at the respective locations for which the variation electrophysiological parameter value is within a predefined consistency criterion range, and automatically discarding from the map the electrophysiological parameters for which the variation electrophysiological parameter value is outside the predefined consistency criterion range.

8. The method according to claim 7, wherein extracting electrophysiological parameters comprises extracting a local-activation-time in a heart of the patient, and computing the measure of consistency comprises computing a measure indicative of a variation of the local-activation-time.

9. The method according to claim 8, wherein computing the measure comprises computing a peak-to-peak variation of the local-activation-time at any given location, and wherein the consistency criterion requires that the peak-to-peak variation of the local-activation-time not exceed a predefined limit.

10. The method according to claim 7, wherein extracting electrophysiological parameters comprises extracting an electrophysiological voltage in a heart of the patient, and computing the respective measure of consistency comprises computing a measure indicative of a variation of the electrophysiological voltage.

11. The method according to claim 10, wherein computing the measure comprises computing a peak-to-peak variation of the electrophysiological voltage at any given location, and wherein the consistency criterion requires that the peak-to-peak variation of the electrophysiological voltage not exceed a predefined limit.

12. The method according to claim 7, wherein displaying the 3D map comprises rendering the 3D map in a background color, and superimposing the visual indication comprises superimposing other colors on the background color at the respective locations indicating respective values of the extracted electrophysiological parameters.

* * * * *